United States Patent [19]
Andersen et al.

[11] Patent Number: 5,198,451
[45] Date of Patent: * Mar. 30, 1993

[54] HETEROCYCLIC CARBOXYLIC ACIDS

[75] Inventors: Knud E. Andersen, Bagsvaerd; Lars J. Stray Knudsen, Vedbaek; Ursula Sonnewald, Trondheim; Per O. Sørensen, Frederiksberg, all of Denmark

[73] Assignee: Novo Nordisk A/S, Bagsvaerd, Denmark

[ * ] Notice: The portion of the term of this patent subsequent to Dec. 10, 2008 has been disclaimed.

[21] Appl. No.: 616,165

[22] Filed: Nov. 20, 1990

[30] Foreign Application Priority Data

Nov. 22, 1989 [DK] Denmark .............................. 5881/89

[51] Int. Cl.$^5$ ................. C07D 211/60; C07D 211/90; A61K 31/445; A61K 31/44
[52] U.S. Cl. .................... 514/330; 514/328; 514/342; 514/354; 514/356; 546/212; 546/213; 546/227; 546/284; 546/318; 546/322; 546/326
[58] Field of Search ............... 546/212, 213, 221, 227, 546/284, 298, 318, 322, 326; 514/328, 330, 342, 356, 354, 350, 327

[56] References Cited

U.S. PATENT DOCUMENTS

| 4,383,999 | 5/1983 | Bondinell | 546/227 |
| 4,772,615 | 9/1988 | Pavia | 546/213 |
| 4,910,312 | 5/1990 | Pavia | 546/227 |
| 5,006,560 | 4/1991 | Kreutner | 514/114 |
| 5,071,859 | 12/1991 | Knudsen | 546/227 |

OTHER PUBLICATIONS

Goodman and Gilman, "The Pharmacological basis of therapeutics", McMillan, 1975, p. 9–10.
Streitwieser and Heathcock, "Introduction to Organic Chemistry", McMillan, 1976, p. 774.

Primary Examiner—C. Warren Ivy
Assistant Examiner—Celia Chang
Attorney, Agent, or Firm—Steve T. Zelson; Elias J. Lambiris

[57] ABSTRACT

Novel N-substituted azaheterocyclic carboxylic acids and esters thereof in which a substituted alkyl chain forms part of the N-substituent, the compounds thus having the general formula I $$Y-(CH_2)_s-X-(CH_2)_r-N\begin{array}{c}R^5\\ \diagup\\ \diagdown R^4\\ \diagdown\\ O\diagdown R^6\end{array} \quad (I)$$

wherein Y is $$\begin{array}{c}R^1\\ \diagdown\\ CH-CH_2-,\\ R^2\diagup\end{array} \quad \begin{array}{c}R^1\\ \diagdown\\ C=CH-\\ R^2\diagup\end{array} \text{ or } \begin{array}{c}R^1\\ \diagdown\\ N-CH-\\ R^2\diagup\end{array}$$

wherein
$R^1$ and $R^2$ independently are $C_{3-8}$ cycloalkyl phenyl or thienyl all of which may be optionally substituted with halogen, trifluoromethyl, $C_{1-16}$ alkyl or $C_{1-6}$ alkoxy;
s is 1, 2 or 3;
x is $-CH_2-$, $-O-$ or $$-\overset{|}{\underset{}{N}}-R^3$$

—wherein $R^3$ is hydrogen or $C_{1-6}$-alkyl;
r is 2, 3 or 4; $R^4$ and $R^5$ each represents hydrogen or may together represent a bond and $R^6$ is OH or $C_{1-8}$-alkoxy; and pharmaceutically acceptable acid addition salts are potent inhibitors of GABA uptake from the synaptic cleft.

13 Claims, No Drawings

HETEROCYCLIC CARBOXYLIC ACIDS

FIELD OF THE INVENTION

The present invention relates to novel N-substituted azaheterocyclic carboxylic acids and esters thereof in which a substituted alkyl chain forms part of the N-substituent and salts thereof, to methods for their preparation, to compositions containing them, and to their use for the clinical treatment of abnormal function of the γ-aminobutyric acid neurotransmission system.

BACKGROUND OF THE INVENTION

In recent years much pharmacological research concerning γ-aminobutyric acid (hereinafter designated GABA), an inhibitory neurotransmitter in the mammalian central nervous system, has been carried out.

The inhibition of GABA uptake results in enhanced availability of this inhibitory neurotransmitter in the synaptic cleft and thus to increased GABA'ergic activity. Increased GABA'ergic activity can be useful in the treatment, for example, of anxiety, pain and epilepsy as well as muscular and movement disorders (see, for example, P. Krogsgaard-Larsen et al., Progress in Medicinal Chemistry, 22 (1985) 68–112).

A well-known and potent inhibitor of GABA uptake from the synaptic cleft into presynaptic nerve terminals and glial cells is, for example, piperidine-3-carboxylic acid (nipecotic acid). However, being a relatively polar compound and therefore unable to cross the blood-brain barrier, piperidine-3-carboxylic acid itself has found no practical utility as a drug.

In U.S. Pat. No. 4,383,999 and No. 4,514,414 (Smith-Kline Beckman Corporation) and in EP 236342 as well as in EP 231996 (Novo Industri A/S) some derivatives of N-(4,4-disubstituted-3-butenyl)-azaheterocyclic carboxylic acids are claimed as inhibitors of GABA uptake. In EP 342635 and EP 374801, respectively (Novo Industri A/S) N-substituted azaheterocyclic carboxylic acids in which an oxime ether group and vinyl ether group forms part of the N-substituent are claimed as inhibitors of GABA uptake. EP 221572 (Warner-Lambert Company) claims that 1-aryloxyalkylpyridine-3-carboxylic acids are inhibitors of GABA uptake.

According to Yunger, L. M. et al., J. Pharm. Exp. Therap. 228 (1984) 109, N-(4,4-diphenyl-3-buten-1-yl)nipecotic acid (designated SK&F 89976A), N-(4,4-diphenyl-3-buten-1-yl)guvacine (designated SK&F 100330A), N-(4,4-diphenyl-3-buten-1-yl)homo-β-proline (designated SK&F 100561) and N-(4-phenyl-4-(2-thienyl)-3-buten-1-yl)nipecotic acid (designated SK&F 100604J) are orally active inhibitors of GABA uptake. These data are summarized in Krogsgaard-Larsen, P. et al., Epilepsy Res. 1 (1987) 77–93.

Guvacine is 1,2,5,6-tetrahydropyridine-3-carboxylic acid.

DESCRIPTION OF THE INVENTION

The present invention relates to novel N-substituted azaheterocyclic carboxylic acids and esters thereof in which a substituted alkyl chain forms part of the N-substituent. The compounds according to the invention have the general formula I

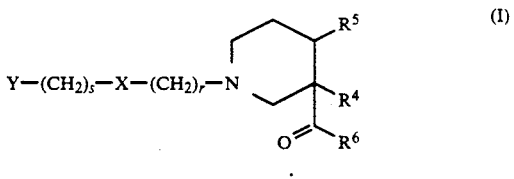

wherein Y is

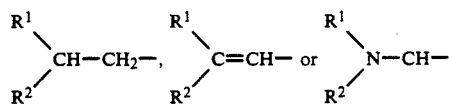

wherein $R^1$ and $R^2$ independently are $C_{3-8}$ cycloalkyl phenyl or thienyl all of which may be optionally substituted with halogen, trifluoromethyl, $C_{1-6}$ alkyl or $C_{1-6}$ alkoxy; s is 1, 2 or 3; X is $-CH_2-$, $-O-$ or

wherein $R^3$ is hydrogen or $C_{1-6}$-alkyl; r is 2, 3 or 4; $R^4$ and $R^5$ each represents hydrogen or may together represent a bond and $R^6$ is OH or $C_{1-8}$-alkoxy.

The compounds of formula I may exist as geometric and optical isomers and all isomers and mixtures thereof are included herein. Isomers may be separated by means of standard methods such as chromatographic techniques or fractional crystallization of suitable salts.

The compounds according to the invention may optionally exist as pharmaceutically acceptable acid addition salts or—when the carboxylic acid group is not esterified—as pharmaceutically acceptable metal salts or— optionally alkylated—ammonium salts.

Pharmaceutically acceptable acid addition salts of compounds of formula I include those derived from inorganic or organic acids such as hydrochloric, hydrobromic, sulfuric, phosphoric, acetic, lactic, maleic, phthalic, citric and fumaric acid.

The compounds of formula I have a greater lipophilicity—and thus a greater availability to the brain—as well as a far higher affinity to the GABA uptake sites than the parent compounds without the N-substituent (i.e. piperidine-3-carboxylic acid (nipecotic acid) and 1,2,5,6-tetrahydropyridin-3-carboxylic acid (guvacine)). They therefore may possess interesting and useful pharmacological properties.

It has been demonstrated that the novel compounds of the general formula I which inhibit the uptake of GABA from the synaptic cleft possess useful pharmacological properties in the central nervous system, in that they cause a selective enhancement of GABA'ergic activity. Compounds of formula I may be used to treat, for example, pain, anxiety, extrapyrimidinal dyskinesia, epilepsy and certain muscular and movement disorders. They may also find use as sedatives, hypnotics and antidepressants.

The compounds having the general formula I may be prepared by the following methods:

Method A:

Reacting a compound of formula II

$Y-(CH_2)_2-X-(CH_2)_4-Z$      (II)

wherein Y, r, s and X are as defined above and Z is a suitable leaving group such as halogen, p-toluene sulphonate or mesylate with an azaheterocyclic compound of formula III

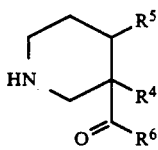

(III)

wherein $R^4$, $R^5$ and $R^6$ are as defined above to form a compound of formula I. This alkylation reaction may be carried out in a solvent such as acetone, dibutylether, 2-butanone, tetrahydrofuran or toluene in the presence of a base e.g. potassium carbonate and a catalyst, e.g. an alkali metal iodide at a temperature up to reflux temperature for the solvent used for e.g. 1 to 120 h.

Method B:

Compounds of general formula I, in which $R^4$ and $R^5$ do not represent a bond and Y represents

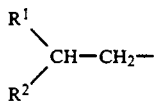

may also be prepared from a compound of formula IV:

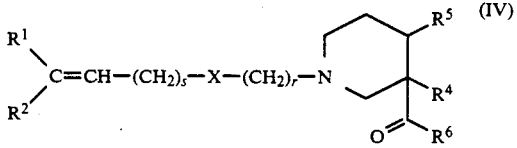

(IV)

wherein $R^1$, $R^2$, $R^4$, $R^5$, $R^6$, r, s and X are as defined above by hydrogenation. This hydrogenation may be carried out in a solvent (e.g. methanol) in the presence of a catalyst (e.g. palladium on carbon) at a pressure of e.g. 1 to 10 atm. for e.g. 0.5 to 18 h.

Compounds of formula II and IV may readily be prepared by methods familiar to those skilled in the art.

Under certain circumstances it may be necessary to protect the intermediates used in the above methods e.g. a compound of formula III with suitable protecting groups. The carboxylic acid group can for example be esterified. Introduction and removal of such groups is described in "Protective Groups in Organic Chemistry" J. F. W. McOrnie ed. (New York, 1973).

If esters have been prepared in methods A and B compounds of formula I wherein $R^6$ is OH may be prepared by hydrolysis of the ester group, preferably at room temperature in a mixture of an aqueous alkali metal hydroxide solution and an alcohol such as methanol or ethanol, for example, for about 0.5 to 6 h.

Pharmacological Methods

Values for in vitro inhibition of [$^3$H]-GABA uptake for these compounds were assessed essentially by the method of Fjalland (Acta Pharmacol.Toxicol. 42 (1978) 73–76).

Male Wistar rat cortical tissue was gently homogenized by hand using a glass/PTFE homogenizer in 10 volumes of 0.32 M sucrose. Incubation was performed in a 40 mM tris HCl buffer (pH 7.5 at 30° C.) containing 120 nM NaCl, 9.2 nM KCl, 4 mM MgSO$_4$, 2.3 mM CaCl$_2$ and 10 mM glucose, for 60 min. at 30° C.)

Values for inhibition of GABA uptake for some representative compounds are recorded in Table I.

TABLE I

| Inhibition of [$^3$H]-GABA uptake | |
|---|---|
| Ex. no. | IC$_{50}$ (nM) in vitro |
| 2 | 108 |
| 4 | 670 |
| 8 | 222 |
| 14 | 51 |
| 16 | 49 |
| 18 | 43 |
| 22 | 251 |
| 28 | 69 |
| 31 | 47 |
| 34 | 75 |

Compounds of formula I are useful because they may possess significant pharmacological activity in man. In particular the compounds of formula I are useful as a consequence of their inhibition of GABA uptake.

For the above indications the dosage will vary depending on the compound of formula I employed, on the mode of administration and on the therapy desired. However, in general, satisfactory results are obtained with a dosage of from about 0.5 mg to about 1000 mg, preferably from about 1 mg to about 500 mg of compounds of formula I, conveniently given from 1 to 5 times daily, optionally in sustained release form. Usually, dosage forms suitable for oral administration comprise from about 0.5 mg to about 1000 mg, preferably from about 1 mg to about 500 mg of the compounds of formula I admixed with a pharmaceutical carrier or diluent. No toxic effects have been observed.

The compounds of formula I may be administered in pharmaceutically acceptable acid addition salt form or where possible as a metal or a lower alkylammonium salt. Such salt forms exhibit approximately the same order or activity as the free base forms.

This invention also relates to pharmaceutical compositions comprising a compound of formula I or a pharmaceutically acceptable salt thereof and, usually, such compositions also contain a pharmaceutical carrier or diluent. The compositions containing the compounds of this invention may be prepared by conventional techniques and appear in conventional forms, for example capsules, tablets, solutions or suspensions.

The pharmaceutical carrier employed may be a conventional solid or liquid carrier. Examples of solid carriers are lactose, terra alba, sucrose, talc, gelatin, agar, pectin, acacia, magnesium stearate and stearic acid. Examples of liquid carriers are syrup, peanut oil, olive oil and water.

Similarly, the carrier or diluent may include any time delay material known to the art, such as glyceryl monostearate or glyceryl distearate, alone or mixed with a wax.

If a solid carrier for oral administration is used, the preparation can be tabletted, placed in a hard gelatin capsule in powder or pellet form or it can be in the form of a troche or lozenge. The amount of solid carrier will vary widely but will usually be from about 25 mg to about 1 g. If a liquid carrier is used, the preparation may be in the form of a syrup, emulsion, soft gelatin capsule or sterile injectable liquid such as an aqueous or nonaqueous liquid suspension or solution.

Generally, the compounds of this invention are dispensed in unit dosage form comprising 50-200 mg of active ingredient in or together with a pharmaceutically-acceptable carrier per unit dosage.

The dosage of the compounds according to this invention is 1-500 mg/day, e.g. about 100 mg per dose, when administered to patients, e.g. humans, as a drug.

A typical tablet which may be prepared by conventional tabletting techniques contains:

| Core: | |
|---|---|
| Active compound (as free compound or salt thereof) | 100 mg |
| Colloidal silicon dioxide (Areosil ®) | 1.5 mg |
| Cellulose, microcryst. (Avicel ®) | 70 mg |
| Modified cellulose gum (Ac-Di-Sol ®) | 7.5 mg |
| Magnesium stearate | |
| Coating: | |
| HPMC approx. | 9 mg |
| *Mywacett ® 9-40 T approx. | 0.9 mg |

*Acylated monoglyceride used as plasticizer for film-coating

The route of administration may be any route which effectively transports the active compound to the appropriate or desired site of action, such as oral or parenteral, the oral route being preferred.

EXAMPLES

The process for preparing compounds of formula I and preparations containing them is further illustrated in the following examples, which, however, are not to be construed as limiting.

Herinafter, TLC is thin layer chromatography, THF is tetrahydrofuran, $CDCl_3$ is deuterio chloroform and DMSO-$d_6$ is hexadeuterio dimethylsulfoxide. The structures of the compounds are confirmed by elemental analysis and NMR, where peaks assigned to benzhydrylic, allylic and vinylic protons in the title compounds are presented where appropriate. NMR spectra were run on a Bruker WM 400 MHz apparatus using tetramethylsilane as reference. M.P. is melting point and is given in °C. HPLC analysis was performed using three reverse phase systems, A: a 5 μm C18 4×200 mm column eluting with a 35-80% gradient of 0.1% TFA/acetonitrile and 0.1% TFA/water over 30 minutes and T=25° C.; B: a 5 μm C18 4×250 mm column eluting with a 30-50% gradient of acetonitrile and 0.1 M ammonium sulphate buffer solution (pH 3.3) over 25 minutes and T=35° C.; C: a 5 μm C18 4×250 mm reverse phase column eluting with 50% acetonitrile and 0.1 M ammonium sulphate buffer solution (pH 3.3) over 30 minutes and T=35° C. TFA is trifluoroacetic acid. Column chromatography was carried out using the technique described by W. C. Still et al, J. Org. Chem. 43, (1978) 2923-2925 on Merck silica gel 60 (Art. 9385). Compounds used as starting materials are either known compounds or compounds which can readily be prepared by methods known per se.

EXAMPLE 1

(R)-N-(2-(2-(Diphenylamino)ethoxy)ethyl)-3-piperidinecarboxylic acid ethyl ester (Method A)

A mixture of sodium hydride (0.70 g, 0.023 mol, 80% oil dispersion) and diphenylamine (3.4 g, 0.020 mol) in dry dibutylether (30 ml) was heated at reflux temperature for 1 h under an atmosphere of nitrogen. The reaction mixture was cooled to 50° C. and 2,2'-dichlorodiethylether (10 ml) was added and the mixture was heated at reflux temperature for 16 h. The reaction mixture was cooled, filtered and the volatile components were removed in vacuo leaving 4.6 g of crude 2-chloro-1-(2-(diphenylamino)ethoxy)ethane as an oil. This oil was dissolved in dry dibutylether (10 ml) and ethyl (R)-3-piperidinecarboxylate (3.7 g, 0.024 mol) and potassium carbonate (3.3 g, 0.024 mol) were added. The mixture was heated at reflux temperature for 2 h under an atmosphere of nitrogen and then stirred overnight at room temperature. Ethyl acetate (50 ml) was added, the mixture was filtered and the solvent was evaporated in vacuo. The residue was submitted to flash chromatography on silica gel (150 g) using a mixture of n-heptane and THF (4:1) as eluent. This provided 3.8 g (48% calculated from diphenylamine) of the title compound as an oil. TLC: rf=0.22 ($SiO_2$; n-heptane/THF=7:3).

EXAMPLE 2

(R)-N-(2-(2-(Diphenylamino)ethoxy)ethyl)-3-piperidinecarboxylic acid hydrochloride The ester prepared in Example 1 (3.5 g, 8.8 mmol) was dissolved in ethanol (10 ml) and a 12 N sodium hydroxide solution (1.5 ml) was added. The reaction mixture was stirred at room temperature for 5 h. A concentrated hydrochloric acid solution (2.2 ml) was added with cooling of the reaction vessel in an ice-bath and dichloromethane (300 ml) was added. The resulting emulsion was dried over sodium sulphate and the solvent evaporated in vacuo to give a residue which was crystallised from acetone. This afforded 1.5 g (43%) of the title compound.

M.P. 145°-148° C. Calculated for $C_{22}H_{28}ClN_2O_3 \cdot 1\text{-}H_2O$: C, 64.9%; H, 7.2%; Cl, 8.8%; N, 6.9%; Found: C, 64.6%; H, 7.4%; Cl, 9.0%; N, 6.7%.

EXAMPLE 3

(R)-N-(6-(Diphenylamino)-1-hexyl)-3-piperidinecarboxylic acid ethyl ester

A mixture of sodium hydride (0.7 g, 0.023 mol, 80% oil dispersion) and diphenylamine (3.4 g, 0.020 mol) in dry dibutylether (30 ml) was heated at reflux temperature for 1 h under an atmosphere of nitrogen. The reaction mixture was cooled and 1,6-dibromohexane (3.1 ml) was added. The mixture was heated at reflux temperature for 3 h and then cooled to 40° C. Ethyl (R)-3-piperidinecarboxylate (3.5 g, 0.022 mol) and potassium carbonate (3.1 g, 0.022 mol) were added and the mixture was heated at reflux temperature for 16 h under an atmosphere of nitrogen. Ethyl acetate (50 ml) was added, the mixture was filtered and the solvent was evaporated in vacuo. The residue was submitted to flash chromatography on silica gel (200 g) using a mixture of n-heptane and THF (4:1) as eluent. This provided 3.4 g (42% calculated from diphenylamine) of the title compound as an oil. TLC: rf=0.26 ($SiO_2$; n-heptane/THF=7:3).

EXAMPLE 4

(R)-N-(6-(Diphenylamino)-1-hexyl)-3-piperidinecarboxylic acid hydrochloride

The ester prepared in Example 3 (3.4 g, 8.3 mmol) was dissolved into ethanol (10 ml) and a 12 N sodium hydroxide solution (1.5 ml) was added. The reaction mixture was stirred at room temperature for 6 h. A concentrated hydrochloric acid solution (2.3 ml) was added with cooling of the reaction vessel in an ice-bath and dichloromethane (300 ml) was added. The resulting emulsion was dried over sodium sulphate and the solvent evaporated in vacuo to give a residue which was crystallised from ethyl acetate. This afforded 2.8 g (81% of the title compound.

M.P. 143°–146° C. Calculated for $C_{24}H_{33}ClN_2O_2$: C, 69.1%; H, 8.0%; Cl, 8.5%; N, 6.7%; Found: C, 69.2%; H, 8.2%; Cl, 8.6%; N, 6.5%.

The compounds in Examples 5–9 were prepared by methods similar to those described in Examples 3 and 4.

EXAMPLE 5

(R)-N-(3-(Diphenylamino)-1-propyl)-3-piperidinecarboxylic acid hydrochloride

M.P. 146°–151° C. Calculated for $C_{21}H_{27}ClN_2O_2$: C, 67.3%; H, 7.3%; Cl, 9.5%; N, 7.5%; Found: C, 67.1%; H, 7.4%; Cl, 9.4%; N, 7.5%.

EXAMPLE 6

(R)-N-(4-(Diphenylamino)-1-butyl)-3-piperidinecarboxylic acid hydrochloride

M.P. 196°–198° C. Calculated for $C_{22}H_{29}ClN_2O_2$: C, 67.9%; H, 7.5%; Cl, 9.1%; N, 7.2%; Found: C, 67.7%; H, 7.7%; Cl, 8.9%; N, 7.0%.

EXAMPLE 7

(R)-N-(5-(Diphenylamino)-1-pentyl)-3-piperidinecarboxylic acid hydrochloride

M P. 175°–178° C. Calculated for $C_{23}H_{31}ClN_2O_2$: C, 68.2%; H, 7.8%; Cl, 8.8%; N, 6.9%; Found: C, 67.8%; H, 7.8%; Cl, 8.7%; N, 6.6%.

EXAMPLE 8

(R)-N-(7-(Diphenylamino)-1-heptyl)-3-piperidinecarboxylic acid hydrochloride

M.P. 115°–120° C. Calculated for $C_{25}H_{35}ClN_2O_2$: C, 69.7%; H, 8.2%; Cl, 8.2%; N, 6.5%; Found: C, 69.5%; H, 8.3%; Cl, 8.2%; N, 6.4%.

EXAMPLE 9

(R)-N-(8-(Diphenylamino)-1-octyl)-3-piperidinecarboxylic acid hydrochloride

M.P. 80°–86° C. Calculated for $C_{26}H_{37}ClN_2O_2$: C, 70.2%; H, 8.4%; Cl, 8.0%; N, 6.3%; Found: C, 69.8%; H, 8.5%; Cl, 7.8%; N, 6.2%.

EXAMPLE 10

(R)-N-(4-(2-Diphenylamino)ethoxy)-1-butyl)-3-piperidinecarboxylic acid hydrochloride 3,4-Dihydro-2H-pyran (92.5 g, 1.1 mol) was added dropwise to 2-bromoethanol (125 g, 1.0 mol) on an ice-bath. The temperature was kept between 25°–30° C. during addition. When addition was complete a concentrated hydrochloric acid solution (1 ml) was added and the reaction mixture was stirred overnight at room temperature. The mixture was fractionated in vacuo to give 147 g (70%) of 2-bromoethyl tetrahydropyran-2-yl ether.

A mixture of sodium hydride (2.0 g, 0.050 mol, 60% oil dispersion), diphenylamine (7.6 g, 0.045 mol) and dry diethylene glycol dimethyl ether (30 ml) was stirred for 3 h at 135° C. under a nitrogen atmosphere. The reaction mixture was cooled using an ice-bath and 2-bromoethyltetrahydropyran-2-yl ether (10.5 g, 0.050 mol) and dry dibutylether (15 ml) were introduced and then the mixture was stirred for 3 h at 120° C. The mixture was cooled, poured into water (300 ml) and extracted with ethyl acetate (2×200 ml). The combined organic extracts was dried over sodium sulphate and the solvent was evaporated in vacuo. The residue was dissolved in isopropanol (150 ml) and a 4 N sulfuric acid solution (30 ml) was added. The mixture was stirred at 60° C. for 30 minutes and the pH was adjusted to 7 with a 4 N sodium hydroxide solution. The neutralised mixture was poured into water (1 l) and extracted with ethyl acetate (2×250 ml). The combined organic extracts was dried over sodium sulphate and the solvent was evaporated in vacuo. The residue was submitted to flash chromatography on silica gel (200 g) using a mixture of n-heptane and THF (4:1) as eluent. This afforded 5.4 g (56%) of 2-(diphenylamino)ethanol.

Sodium hydride (0.4 g, 10.0 mmol, 60% oil dispersion) was suspended in dry dibutylether (25 ml) and under an atmosphere of nitrogen 2-(diphenylamino)ethanol (2.1 g, 10.0 mmol) was added. The mixture was stirred for 1 h at room temperature and then heated at 130° C. for 1 h. Lithium hydride (0.1 g) was added and the mixture was heated at reflux temperature for 1 h. The mixture was cooled to 80° C. and 1-bromo-4-chlorobutane (2.0 g, 11.7 mmol) was added. The reaction mixture was heated at reflux temperature for 12 h and then another portion of 1-bromo-4-chlorobutane (4.0 g, 23.4 mmol) was added. Heating was continued for further 24 h. Dibutylether (25 ml) was added to the cooled reaction mixture and then water (25 ml) was added carefully. The organic phase was separated, dried over potassium carbonate and the solvent was evaporated in vacuo. The residue was submitted to flash chromatography on silica gel (100 g) using a mixture of n-heptane and THF (4:1) as eluent. This afforded 2.0 g of 1-chloro-4-(2-(diphenylamino)ethoxy)butane.

A mixture of 1-chloro-4-(2-(diphenylamino)ethoxy)-butane (2.0 g, 6.6 mmol), ethyl (R)-3-piperidinecarboxylate (1.1 g, 7.0 mmol), potassium carbonate (1.0 g, 7.2 mmol) and dry dibutylether was heated at 150° C. for 4 h. The mixture was cooled, filtered and the solvent evaporated in vacuo. The residue was submitted to flash chromatography on silica gel (150 g) using a mixture of n-heptane and THF (4:1) as eluent. This afforded 1.5 g (34% calculated from 2- (diphenylamino)ethanol) of (R)-N-(4-(2-(diphenylamino)ethoxy)-1-butyl)-3-piperidinecarboxylic acid ethyl ester as an oil. TLC: rf=0.23 ($SiO_2$; n-heptane/THF=7:3).

(R)-N-(4-(2-(Diphenylamino)ethoxy)-1-butyl)-3-piperidinecarboxylic acid ethyl ester (1.5 g, 3.5 mmol) was dissolved into ethanol (10 ml) and a 12 N sodium hydroxide solution (0.85 ml) was added. The reaction mixture was stirred at room temperature for 3 h. A concentrated hydrochloric acid solution (1.7 ml) was added with cooling of the reaction vessel in an ice-bath and dichloromethane (300 ml) was added. The resulting emulsion was dried over sodium sulphate and the solvent evaporated in vacuo to give a residue which was crystallised from acetone. This afforded 1.1 g (73%) of the title compound.

HPLC retention time=26.9 minutes (system A). Calculated for $C_{24}H_{33}ClN_2O_3$: C, 66.6%; H, 7.7%; Cl, 8.2%; N, 6.5%; Found: C, 66.6%; H, 7.7%; Cl, 8.4%; N, 6.3%.

The compounds in Example 11 and 12 were prepared by a method similar to that described in Example 10.

EXAMPLE 11

(R)-N-(3-(3-Diphenylamino-1-propyloxy)-1-propyl)-3-piperidine carboxylic acid hydrochloride M.P. 138°–140° C. Calculated for $C_{24}H_{33}ClN_2O_3$: C, 66.6%; H, 7.7%; Cl, 8.2%; N, 6.5%; Found: C, 66.9%; H, 7.8%; Cl, 8.2%; N, 6.4%

EXAMPLE 12

(R)-N-(2-(4-Diphenylamino-1-butyloxy)ethyl)-3-piperidine carboxylic acid hydrochloride HPLC retention time = 27.0 minutes (system A).

EXAMPLE 13

(R)-N-(2-(3,3-Diphenyl-1-propyloxy)ethyl)-3-piperidinecarboxylic acid ethyl ester A mixture of sodium hydride (0.80 g, 0.020 mol, 60% oil dispersion) and 3,3-diphenyl-1-propanol (4.25 g, 0.020 mol) in dry dibutylether (30 ml) was stirred at room temperature for 30 minutes and then heated at reflux temperature for 2.5 h under an atmosphere of nitrogen. The reaction mixture was cooled to 60° C. and 2-bromoethyltetrahydro-2-pyranyl ether (4.2 g, 0.020 mol) was added. The mixture was heated at reflux temperature for 16 h under an atmosphere of nitrogen. The reaction mixture was cooled, washed with water and the organic solvent was evaporated in vacuo. Flash chromatography of the residue on silica gel (150 g) using a mixture of n-heptane and THF (4:1) as eluent provided 2.6 g of an oil, which was dissolved in isopropanol (25 ml). A 4 N sulfuric acid solution (10 ml) was added and the mixture was stirred at 60° C. for 1 h. Dichloromethane (250 ml) was introduced and the separated organic phase was washed with water (2 × 100 ml) and a 5% sodium bicarbonate solution (100 ml). The organic phase was dried over sodium sulphate and the solvent was evaporated in vacuo to give 2.5 g (49%) of 2-(3,3-diphenyl-1-propyloxy)ethanol as an oil.

A solution of 2-(3,3-diphenyl-1-propyloxy)ethanol (2.5 g, 0.010 mol) in dry THF (20 ml) was placed on an ice-bath and a solution of n-butyllithium in hexanes (4.0 ml, 2.5 M) was added dropwise under an atmosphere of nitrogen. When addition was complete the reaction mixture was stirred at room temperature for 0.5 h and then heated at reflux temperature for 1 h. The mixture was cooled to room temperature and p-toluenesulphonyl chloride (2.1 g, 0.011 mol) was added. The mixture was stirred at room temperature for 0.5 h and then heated at reflux temperature for 1 h. To the cooled reaction mixture was added dry potassium carbonate (2.0 g, 0.015 mol) and ethyl (R)-3-piperidinecarboxylate (2.0 g, 0.0125 mol) and the mixture was heated at reflux temperature for 3 h. The cooled reaction mixture was poured into water (200 ml) and extracted with ethyl acetate (2 × 200 ml). The combined organic extracts was dried over sodium sulphate and the solvent evaporated in vacuo. The residue was submitted to flash chromatography on silica gel (150 g) using a mixture of n-heptane and THF (4:1) as eluent. This provided 0.9 g (11% calculated from 3,3-diphenyl-1-propanol) of the title compound as an oil. TLC: rf=0.24 (SiO$_2$; n-heptane/THF=7:3). $^1$H NMR $\delta$ (CDCl$_3$) 4.10 (t, 1H).

EXAMPLE 14

(R)-N-(2-(3,3-Diphenyl-1-propyloxy)ethyl)-3-piperidinecarboxylic acid hydrochloride The ester prepared in Example 13 (0.9 g, 2.3 mmol) was dissolved in ethanol (10 ml) and a 12 N sodium hydroxide solution (0.6 ml) was added. The reaction mixture was stirred at room temperature for 4 h. Concentrated hydrochloric acid solution (0.7 ml) was added with cooling of the reaction vessel in an ice-bath and dichloromethane (300 ml) was added. The resulting emulsion was dried over sodium sulphate and the solvent evaporated in vacuo to give an oily residue which was crystallised from acetone. This afforded 0.5 g (54%) of the title compound.

M.P. 178°–179° C. Calculated for $C_{23}H_{30}ClNO_3$: C, 68.4%; H, 7.5%; Cl, 8.8%; N, 3.5%; Found: C, 67.9%; H, 7.5%; Cl, 8.8%; N, 3.3%

$^1$H NMR (DMSO-d$_6$)$\delta$ 4.12 (t, 1H).

EXAMPLE 15

N-(2-(3,3-Diphenyl-1-propyloxy)ethyl)-1,2,5,6-tetrahydro-3-pyridinecarboxylic acid ethyl ester A solution of n-butyllithium in hexanes (20 ml, 2.5 M) was added dropwise under a nitrogen atmosphere to dry ethylene glycol (40 ml) at 10° C. When addition was complete the mixture was stirred for 0.5 h at room temperature. 3-Bromo-1,1-diphenyl-1-propene (13.7 g, 50 mmol, prepared similarly to the method described in Example 23) was added and the reaction mixture was stirred at room temperature for 48 h. The mixture was poured into water (100 ml) and extracted with ethyl acetate (2 × 100 ml). The combined organic extracts was dried over sodium sulphate and the solvent evaporated in vacuo. Flash chromatography of the residue on silica gel (150 g) using a mixture of cyclohexane and ethyl acetate (7:3) as eluent provided 6.2 g (48%) of 2-(3,3-diphenyl-3-propen-1-yloxy)ethanol.

2-(3,3-Diphenyl-3-propen-1-yloxy)ethanol (4.0 g, 15.7 mmol) was dissolved in dry dioxan (80 ml) and stirred under an atmosphere of hydrogen for 3 h at room temperature in the presence of 10% palladium on carbon catalyst (50% aqueous paste) and then filtered. The solvent was evaporated in vacuo to give 4.0 g (100%) of 2-(3,3-diphenyl-1-propyloxy)ethanol.

A solution of 2-(3,3-diphenyl-1-propyloxy)ethanol (3.9 g, 15 mmol) in dry THF (30 ml) kept under a nitrogen atmosphere was cooled to 10° C. and a solution of n-butyllithium in hexanes (6.0 ml, 2.5 M) was added dropwise. The reaction mixture was stirred for 1 h at room temperature and heated at reflux temperature for 1.5 h and then cooled to room temperature. p-Toluenesulphonyl chloride (2.9 g, 15 mmol) was added and the mixture was stirred at room temperature for 1.5 h. Ethyl 1,2,5,6-tetrahydro-3-pyridinecarboxylate hydrochloride (3.8 g, 20 mmol) and potassium carbonate (5.0 g, 38 mmol) were added and the mixture was stirred at room temperature for 0.5 h and then heated at reflux temperature for 4 h. The reaction mixture was allowed to stand overnight and was diluted with ice water (25 ml) and ethyl acetate (100 ml). The separated organic phase was extracted with a 10% citric acid solution (4 × 50 ml) and the combined aqueous extracts was washed with ethyl acetate (25 ml). The acidic aqueous phase was adjusted to pH 5 with a sodium bicarbonate solution and extracted with ethyl acetate. The organic extract was washed with a diluted sodium bicarbonate solution, dried over sodium sulphate and the solvent evaporated in vacuo to give 1.9 g (32%) of the title compound as an oil. TLC: rf=0.21 (SiO2; n-heptane/THF=7:3). $^1$H NMR (CDCl3)δ 4.12 (t, 1H); 7.00 (m, 1H).

EXAMPLE 16

N-(2-(3,3-Diphenyl-1-propyloxy)ethyl)-1,2,5,6-tetrahydro-3-pyridinecarboxylic acid hydrochloride The ester prepared in Example 15 (1.9 g, 4.8 mmol) was dissolved in ethanol (10 ml) and a 12 N sodium hydroxide solution (1.0 ml) was added. The reaction mixture was stirred at room temperature for 5 h. A concentrated hydrochloric acid solution (1.5 ml) was added with cooling of the reaction vessel in an ice-bath and dichloromethane (500 ml) was added. The resulting emulsion was dried over sodium sulphate and the solvent evaporated in vacuo to give an oily residue which was stripped twice with acetone and crystallised from ethyl acetate. This afforded 1.5 g (78%) of the title compound as a crystalline solid.

M.P. 155°–156° C. Calculated for $C_{23}H_{28}ClNO_3$: C, 68.7%; H, 7.0%; Cl, 8.8%; N, 3.5% Found: C, 68.2%; H, 7.2%; Cl, 8.8%; N, 3.4%

$^1$H NMR (DMSO-d6)δ 4.13 (t, 1H); 7.02 (m, 1H).

EXAMPLE 17

(R)-N-(2-(3-Phenyl-3-(3-(trifluoromethyl)phenyl)-1-propyloxy)ethyl)-3-piperidinecarboxylic acid ethyl ester A solution of n-butyllithium in hexanes (16 ml, 2.5 M) was added dropwise under a nitrogen atmosphere to dry ethylene glycol (40 ml) at 10° C. When addition was complete the mixture was stirred for 0.5 h at room temperature. 3-Bromo-1-phenyl-1-(3-(trifluoromethyl)-phenyl)-1-propene (12.0 g, 35 mmol, prepared similarly to the method described in Example 23) was added and the reaction mixture was stirred at room temperature for 72 h. The mixture was poured into water (300 ml) and extracted with ethyl acetate (2×100 ml). The combined organic extracts was dried over sodium sulphate and the solvent evaporated in vacuo. Flash chromatography of the residue on silica gel (150 g) using a mixture of cyclohexane and ethyl acetate (7:3) as eluent provided 5.9 g (52%) of 2-(3-phenyl-3-(3-(trifluoromethyl)-phenyl)-2-propen-1-yloxy)ethanol. 2-(3-phenyl-3-(3-(trifluoromethyl)phenyl)-2-propen-1-yloxy) ethanol (5.0 g, 15.5 mmol) was dissolved into dry dioxan (80 ml) and stirred under an atmosphere of hydrogen for 18 h at room temperature in the presence of 10% palladium on carbon catalyst (50% aqueous paste) and then filtered. The filtrate was evaporated in vacuo to give 4.0 g (95%) of 2-(3-phenyl-3-(3-trifluoromethyl)phenyl)-1-propyloxy)ethanol. $^1$H NMR (CDCl3)δ 4.20 (t, 1H).

A solution of 2-(3-phenyl-3-(3-trifluoromethyl)-phenyl)-1-propyloxy)ethanol (4.8 g, 15 mmol) in dry THF (35 ml) kept under a nitrogen atmosphere was cooled to 10° C. and a solution of n-butyllithium in hexanes (6.0 ml, 2.5 M) was added dropwise. The reaction mixture was stirred for 0.5 h at room temperature, heated at reflux temperature for 1 h and cooled to room temperature. p-Toluenesulphonyl chloride (2.9 g, 15 mmol) was added and the mixture was heated at reflux temperature for 1.5 h and then cooled to room temperature. Ethyl (R)-3-piperidinecarboxylate (3.2 g, 20 mmol) and potassium carbonate (2.8 g, 20 mmol) were added and the mixture was heated at reflux temperature for 4.5 h. The reaction mixture was diluted with ice water (100 ml) and ethyl acetate (150 ml). The separated organic phase was washed with a diluted sodium bicarbonate solution, dried over sodium sulphate and the solvent evaporated in vacuo. Flash chromatography of the residue on silica gel (100 g) using a mixture of cyclohexane and ethyl acetate (7:3) as eluent provided 2.4 g (35%) of the title compound as an oil. TLC: rf=0.11 (SiO2; cyclohexane/ethyl acetate=7:3). $^1$H NMR (CDCl3)δ 4.20 (t, 1H).

EXAMPLE 18

(R)-N-(2-(3-Phenyl-3-(3-(trifluoromethyl)phenyl)-1-propyloxy)ethyl)-3-piperidinecarboxylic acid hydrochloride The ester prepared in Example 17 (2.4 g, 5.2 mmol) was dissolved in ethanol (10 ml) and a 12 N sodium hydroxide solution (1.1 ml) was added. The reaction mixture was stirred at room temperature for 4 h. A concentrated hydrochloric acid solution (1.6 ml) was added with cooling on an ice-bath and dichloromethane (400 ml) was added. The resulting emulsion was dried over sodium sulphate and the solvent evaporated in vacuo to give an oily residue which was stripped twice with acetone and dissolved in toluene (50 ml). The organic solution was extracted with water (2×50 ml) and the combined aqueous extracts was washed with ethyl acetate (2×25 ml). Water was evaporated from the aqueous phase in vacuo to give a residue which was stripped with dichloromethane. This afforded 0.8 g (33%) of the title compound as an amorphous solid.

HPLC retention time=11.4 minutes (system A). Calculated for $C_{24}H_{29}ClF_3NO_3$, $H_2O$: C, 58.8%; H, 6.4%; Cl, 7.5%; N, 2.9% Found: C, 58.6%; H, 6.5%; Cl, 7.5%; N, 2.7% $^1$H NMR (DMSO-d6)δ 4.30 (dt, 1H).

EXAMPLE 19

(R)-N-(2-(3,3-Bis(4-Chlorophenyl)-1-propyloxy)ethyl)-3-piperidinecarboxylic acid ethyl ester 2-(3,3-Bis(4-Chlorophenyl)-2-propen-1-yloxy)ethanol (4.5 g, 14.0 mmol, prepared as described in Example 35) was dissolved in dry dioxan (50 ml) and stirred under an atmosphere of hydrogen for 18 h at room temperature in the presence of 10% palladium on carbon catalyst (50% aqueous paste) and then filtered. The solvent was evaporated in vacuo to give an oil which was submitted to flash chromatography on silica gel (100 g) using a mixture of cyclohexane/ethyl acetate (6:4) as eluent. This afforded 3.5 g (78%) of 2-(3,3-bis(4-chlorophenyl)-1-propyloxy)ethanol. TLC: rf=0.40 (SiO2; n-heptane/ethyl acetate=3:7). $^1$H NMR (CDCl3)δ 4.08 (t, 1H).

A solution of 2-(3,3-bis(4-chlorophenyl)-1-propyloxy) ethanol (3.5 g, 10.8 mmol) in dry THF (25 ml) kept under a nitrogen atmosphere was cooled to 10° C. and a solution of n-butyllithium in hexanes (4.3 ml, 2.5 M) was added dropwise. When addition was complete the reaction mixture was stirred for 1 h at room temperature. p-Toluenesulphonyl chloride (2.1 g, 10.8 mmol) was added and the mixture was stirred at room temperature for 1.5 h. The solvent was evaporated in vacuo and acetone (30 ml) was added to the residue. The mixture was filtered and to the filtrate was added ethyl (R)-3-piperidinecarboxylate (1.8 g, 11.5 mmol) and potassium carbonate (1.5 g, 10.8 mmol). The mixture was heated at reflux temperature for 3 h and then stirred for 2 days at room temperature. The reaction mixture was filtered and the solvent was evaporated in vacuo. Flash chromatography of the residue on silica gel (200 g) using a mixture of n-heptane and ethyl acetate (6:4) as eluent provided 2.0 g (40%) of the title compound as an oil. TLC: rf=0.17 (SiO$_2$; n-heptane/ethyl acetate=7.3). $^1$H NMR (CDCl$_3$)δ 4.13 (t, 1H).

EXAMPLE 20

(R)-N-(2-(3,3-Bis(4-Chlorophenyl)-1-propyloxy)ethyl)3-piperidinecarboxylic acid hydrochloride The ester prepared in Example 19 (1.9 g, 4.0 mmol) was dissolved in ethanol (15 ml) and a 4 N sodium hydroxide solution (3.0 ml) was added. The reaction mixture was stirred at room temperature for 4 h. A concentrated hydrochloric acid solution (1.5 ml) was added with cooling on an ice-bath and dichloromethane (400 ml) was added. The phases were separated and the organic phase was dried over sodium sulphate. The solvent was evaporated in vacuo to give an oily residue which was stripped twice with acetone and crystallised from ethyl acetate. This afforded 1.4 g (74%) of the title compound as a crystalline material.

M.P. 165°-167° C.

HPLC retention time=13.7 minutes (system A)

$^1$H NMR (DMSO-d$_6$)δ 4.20 (t, 1H).

EXAMPLE 21

(R)-N-(2-(3,3-Diphenyl-2-propen-1-yloxy)ethyl)-3-piperidinecarboxylic acid ethyl ester (Method B)

To a well-stirred solution of propiophenone (20.1 g, 0.15 mol) in dry diethyl ether (125 ml) kept under nitrogen at room temperature was added a solution of phenylmagnesium bromide (55 ml, 3 M in diethyl ether) in dry diethyl ether (25 ml). The reaction mixture was stirred for 1 h and a mixture of a saturated ammonium chloride solution (100 ml) and water (50 ml) was added. The phases were separated and the aqueous phase was extracted with diethyl ether (100 ml). The combined organic phases was washed with a 0.5 N hydrochloric acid solution and dried over sodium sulphate. The solvent was evaporated in vacuo to give a solid residue which was trituated with cyclohexane (100 ml). The solid was collected by filtration and dried to give 26.4 g (83%) of 1,1-diphenyl-1-propanol.

A mixture of 1,1-diphenyl-1-propanol (64 g, 0.30 mol), isopropanol (300 ml) and a 5 N solution of sulphuric acid (150 ml) was heated at reflux temperature for 18 h. The reaction mixture was cooled, diluted with water (600 ml) and extracted with toluene (3×150 ml). The combined organic phases was dried over sodium sulphate and the solvent was evaporated in vacuo to give a solid residue which was trituated with iso-octane. The solid was collected by filtration to give 28.8 g (49%) of 1,1-diphenyl-1-propene.

A mixture of 1,1-diphenyl-1-propene (17.0 g, 0.10 mol), carbon tetrachloride (100 ml), benzoylperoxide (0.2 g) and N-bromosuccinimide (17.8 g, 0.10 mol) was heated at reflux temperature for 18 h. The reaction mixture was allowed to cool to room temperature, filtered and the solvent was evaporated in vacuo to give 3-bromo-1 1-diphenyl-1-propene in a quantitative yield.

A solution of n-butyllithium in hexanes (7.3 ml, 2.5 M) was added dropwise under a nitrogen atmosphere to ethylene glycol (20 ml) at 10° C. When addition was complete the mixture was stirred for 0.5 h at room temperature. 3-Bromo-1,1-diphenyl-1-propene (5.0 g, 18.3 mmol) was added and the reaction mixture was stirred at room temperature for 1 h, at 80° C. for 0.5 h and finally at room temperature for 3 h. Water (100 ml) was added and the mixture was extracted with ethyl acetate (100 ml). The phases were separated and the organic phase was washed with water (2×50 ml), dried over sodium sulphate and the solvent was evaporated in vacuo. Flash chromatography of the residue on silica gel (150 g) using n-heptane and THF (4:1) as eluent provided 2.9 g (62%) of 2-(3,3-diphenyl-2-propen-1-yloxy)ethanol.

A solution of 2-(3,3-diphenyl-2-propen-1-yloxy)ethanol (3.0 g, 11.8 mmol) in dry THF (30 ml) kept under a nitrogen atmosphere was cooled to 10° C. and a solution of n-butyllithium in hexanes (5.0 ml, 2.5 M) was added dropwise. The reaction mixture was stirred for 0.5 h at room temperature and p-toluenesulphonyl chloride (2.3 g, 12.1 mmol) was added. The mixture was stirred at room temperature for 1 h. Ethyl (R)-3-piperidinecarboxylate (2.7 g, 17.7 mmol) and potassium carbonate (2.5 g, 17.7 mmol) were added and the mixture was heated at reflux temperature for 5 h. The cooled reaction mixture was poured into water (100 ml) and extracted with ethyl acetate (2×75 ml). The combined organic phases was washed with water and a sodium citrate buffer solution (2×100 ml, pH 6). The organic phase was then extracted with a 5% citric acid solution (3×75 ml) and the combined acidic aqueous extracts was washed with ethyl acetate (25 ml). To the acidic aqueous solution was added a 4 N sodium hydroxide solution until pH 11 and this solution was immediately extracted with ethyl acetate (3×50 ml). The combined organic extracts was dried over sodium sulphate and the solvent evaporated in vacuo to give 1.5 g (33%) of the title compound as an oil. TLC: rf=0.20 (SiO$_2$; n-heptane/THF=7:3). $^1$H NMR (CDCl$_3$)δ 4.08 (d, 2H); 6.22 (t, 1H).

EXAMPLE 22

(R)-N-(2-(3,3-Diphenyl-2-propen-1-yloxy)ethyl)-3-piperidinecarboxylic acid hydrochloride The ester prepared in Example 21 (1.4 g, 3.6 mmol) was dissolved in ethanol (10 ml) and a 12 N sodium hydroxide solution (0.9 ml) was added. The reaction mixture was stirred at room temperature for 3.5 h. A concentrated hydrochloric acid solution (2.0 ml) was added with cooling on an ice-bath and dichloromethane (250 ml) was added. The resulting emulsion was dried over sodium sulphate and the solvent evaporated in vacuo to give an oily residue which was agitated with acetone. This afforded 0.85 g (60%) of the title compound as a crystalline solid.

M.P. 160°-165° C.

HPLC retention time=16.6 minutes (system A).

$^1$H NMR (DMSO-d$_6$)δ 4.03 (d, 2H); 6.22 (t, 1H).

EXAMPLE 23

(R)-N-(2-(3-(2-Methylphenyl)-3-phenyl-2-propen-1-yloxy)ethyl)-3-piperidinecarboxylic acid hydrochloride Propiophenone (6.7 g, 50 mmol) was added dropwise to a solution of 2-methylphenylmagnesium chloride (30 ml of a 2.0 M solution in diethyl ether) and dry THF (50 ml) under a nitrogen atmosphere. When the addition was complete the reaction mixture was heated at reflux temperature for 5 h. Excess of a saturated ammonium chloride solution was added and the mixture was extracted with diethyl ether (2×100 ml). The combined organic extracts were dried over potassium carbonate and the solvent was evaporated in vacuo to give 10.4 g (92%) of 1-(2-methyl phenyl)-1-phenyl-1- propanol. TLC: rf=0.50 (SiO$_2$; n-heptane/THF=7:3).

1-(2-Methylphenyl)-1-phenyl-1-propanol (10.4 g, 46 mmol) was dissolved into isopropanol (100 ml) and a 4 N sulphuric acid solution (50 ml) was added. The reaction mixture was heated at reflux temperature for 18 h and cooled to room temperature. Water (300 ml) was added and the mixture was extracted with dichloromethane (2×200 ml). The combined organic extracts was washed with a diluted sodium bicarbonate solution, dried over sodium sulphate and the solvent evaporated in vacuo to give 9.0 g (91% of 1-(2-methylphenyl)-1-phenyl-1-propene.

To a solution of 1-(2-methylphenyl)-1-phenyl-1-propene (9.0 g, 43 mmol) in carbon tetrachloride (40 ml), N-bromosuccinimide (7.7 g, 43 mmol) and benzoylperoxide (0.1 g) were added. The reaction mixture was heated at reflux temperature for 18 h. The cooled reaction mixture was filtered through silica gel and the solvent evaporated in vacuo to give 9.3 g (76%) of 3-bromo-1-(2-methylphenyl)-1-phenyl-1-propene.

A solution of n-butyllithium in hexanes (13.0 ml, 2.5 M) was added dropwise under a nitrogen atmosphere to ethylene glycol (30 ml) at 10° C. When addition was complete the mixture was stirred 0.5 h at room temperature. 3-Bromo-1-(2-methylphenyl)-1-phenyl-1-propene (9.3 g, 32 mmol) was added and the reaction mixture was stirred at room temperature for 100 h. The mixture was poured into water (200 ml) and extracted with ethyl acetate (3×75 ml). The combined organic extracts was dried over sodium sulphate and the solvent evaporated in vacuo. Flash chromatography of the residue on silica gel (200 g) using a mixture of n- heptane and THF (4:1) as eluent provided 3.9 g (45%) of 2-(3-(2-methylphenyl)-3-phenyl-2-propen-1-yloxy)ethanol. TLC: rf=0.20 (SiO$_2$; n-heptane/THF=7:3).

A solution of 2-(3-(2-methylphenyl)-3-phenyl-2-propen-1-yloxy)ethanol (3.4 g, 12.5 mmol) in dry THF (30 ml) kept under a nitrogen atmosphere was cooled to 10° C. and a solution of n-butyllithium in hexanes (5.5 ml, 2.5 M) was added dropwise. The reaction mixture was stirred for 0.5 h at room temperature and p-toluenesulphonyl chloride (2.6 g, 13.8 mmol) was added. The mixture was stirred at room temperature for 1.5 h. Ethyl (R)-3-piperidinecarboxylate (2.9 g, 18.8 mmol) and potassium carbonate (2.6 g, 18.8 mmol) were added and the mixture was heated at reflux temperature for 18 h. The cooled reaction mixture was poured into ice water (200 ml) and extracted with ethyl acetate (2×100 ml). The combined organic extracts was washed with a 10% sodium citrate buffer solution (2×100 ml, pH 6). The organic phase was extracted with a 5% citric acid solution (4×75 ml) and the combined acidic aqueous extracts was washed with toluene (50 ml). To the acidic aqueous solution was added a 4 N sodium hydroxide solution until pH 9 and this solution was immediately extracted with ethyl acetate (2×100 ml). The combined organic extracts was dried over sodium sulphate and the solvent evaporated in vacuo to give 2.3 g (45%) of (R)-N-(2-(2-(2-methylphenyl)-3-phenyl-2-propen-1-yloxy)ethyl)-3-piperidinecarboxylic acid ethyl ester as an oil. TLC: rf=0.23 (SiO$_2$; n-heptane/THF=7:3).

(R)-N-(2-(3-(2-Methylphenyl)-3-phenyl-2-propen-1-yloxy)ethyl)-3-piperidinecarboxylic acid ethyl ester (2.3 g, 5.6 mmol) was dissolved in ethanol (10 ml) and a 12 N sodium hydroxide solution (1.4 ml) was added. The reaction mixture was stirred at room temperature for 4 h. A concentrated hydrochloric acid solution was added with cooling of the reaction vessel in an ice-bath until pH 1 and dichloromethane (250 ml) was added. The resulting emulsion was dried over sodium sulphate and the solvent was evaporated in vacuo to give a residue which was crystallised from acetone. This afforded 1.75 g (76%) of the title compound.

M.P. 145°-150° C. Calculated for C$_{24}$H$_{30}$ClNO$_3$: C, 69.3%; H, 7.3%; Cl, 8.5%; N, 3.4% Found: C, 69.0%; H, 7.4%; Cl, 8.5%; N, 3.4%

$^1$H NMR (DMSO-d$_6$)δ 3.86 (d, 2H); 6.42 (t, 1H).

EXAMPLE 24

(R)-N-(2-(3-(2-Methylphenyl)-3-phenyl-1-propyloxy)-ethyl)-3-piperidinecarboxylic acid hydrochloride The acid prepared in Example 23 (1.0 g, 2.4 mmol) was dissolved in methanol (20 ml) and stirred under an atmosphere of hydrogen for 1 h at room temperature in the presence of 10% palladium on carbon catalyst (50% aqueous paste) and then filtered. The filtrate was evaporated to dryness leaving a residue which was treated with ethyl acetate to give 0.8 g (80 %) of the title compound as a solid.

M.P. 137°-140° C.

HPLC retention time=17.1 minutes (system A).

$^1$H NMR (DMSO-d$_6$)δ 4.30 (t, 1H).

EXAMPLE 25

(R)-N-(2-(3,3-Bis(4-(Trifluoromethyl)phenyl)-2-propen-1-yloxy)ethyl)-3-piperidinecarboxylic acid A solution of n-butyllithium in hexanes (34.2 ml, 2.5 M) was added dropwise under a nitrogen atmosphere to ethylene glycol (8 ml) below 15° C. When addition was complete the mixture was stirred for 1 h at room temperature. A solution of 3-bromo-1,1-bis(4-(trifluoromethyl)phenyl)-1-propene (35 g, 0.086 mol, prepared similarly to the method described in Example 23) in toluene (40 ml) was added and the reaction mixture was stirred at room temperature for 60 h and then at 55° C. for 36 h. Water (300 ml) was added to the cooled reaction mixture and the mixture was extracted with ethyl acetate (250+50 ml). The combined organic extracts was washed with brine and dried over sodium sulphate. The solvent was evaporated in vacuo to give a residue which was stripped with methanol and dichloromethane sucessively. This afforded 33.1 g (99%) of 2-(3,3-bis(4-(trifluoromethyl)phenyl)-2-propen-1-yloxy)ethanol. TLC: rf=0.50 (SiO$_2$: dichloromethane/methanol=19:1).

A mixture of 2-(3,3-bis(4-(trifluoromethyl)phenyl)-2-propen-1-yloxy)ethanol (25.0 g, 64 mmol) and triethylamine (16.2 g, 0.16 mol) in dry toluene (100 ml) kept under a nitrogen atmosphere was cooled to 10° C. and a solution of methanesulphonyl chloride (14.6 g, 0.13 mol) in dry toluene (100 ml) was added dropwise keeping the temperature below 10° C. When addition was complete the reaction mixture was stirred for 45 minutes at 5° C. and then for 30 minutes at 15° C. Water was added (100 ml) and the mixture was stirred at room temperature for 15 minutes. The phases were separated and the aqueous phase was extracted with two small portions of toluene. The combined organic extracts was washed with brine, dried over sodium sulphate and filtered. To the filtrate was added ethyl (R)-3-piperidine carboxylate (20.1 g, 0.13 mol) and potassium carbonate (22.1 g, 0.16 mol) and the mixture was heated at reflux temperature for 2 days and then stirred at room temperature for 2 days. The reaction mixture was filtered and the solvent evaporated in vacuo to give a residue which was dissolved into a mixture of ethyl acetate (125 ml) and water (75 ml). A 10% citric acid solution was added until pH 4 and the phases were separated. The organic phase was evaporated in vacuo to give a residue which was dissolved in toluene (150 ml). A mixture of a 34% citric acid solution (56 ml) and water (150 ml) was added and the phases were separated. The organic phase was extracted once more with a mixture of a 34% citric acid solution (20 ml) and water (50 ml). To the combined aqueous extracts was added ethyl acetate (150 ml) and excess of a 5% aqueous sodium bicarbonate solution. The phases were separated, the organic phase was dried over sodium sulphate and the solvent evaporated in vacuo to give 21.7 g (64%) of (R)-N-(2-(3,3-bis-(4-(trifluoromethyl)phenyl)-2-propen-1-yloxy)ethyl)-3-piperidinecarboxylic acid ethyl ester as an oil. TLC: rf=0.60 (SiO2; dichloromethane/methanol/acetic acid=20:2:1).

(R)-N-(2-(3,3-bis(4-(trifluoromethyl)phenyl)-2-propen-1-yloxy)ethyl)-3-piperidinecarboxylic acid ethyl ester (2.0 g, 3.8 mmol) was dissolved in ethanol (30 ml) and a 1 M sodium hydroxide solution (17 ml) was added. The reaction mixture was stirred at room temperature for 3 h. The solvent was evaporated in vacuo and dichloromethane (100 ml) was added. A concentrated hydrochloric acid solution was added (1.9 ml) and the phases were separated. Ethyl acetate was added to the organic phase which was then dried over sodium sulphate. The solvent was evaporated in vacuo to give 2.0 g (99%) of the title compound as a solid.

HPLC retention time=7.8 minutes (system C).
1H NMR (DMSO-d6)δ 4.07 (d, 2H); 6.50 (t, 1H).

EXAMPLE 26

(R)-N-(2-(3,3-Bis(4-(Trifluoromethyl)phenyl)-1-propyloxy)ethyl)-3-piperidinecarboxylic acid hydrochloride The acid prepared in Example 25 (1.6 g, 3.0 mmol) was dissolved in methanol (45 ml) and stirred under an atmosphere of hydrogen for 1 h at room temperature in the presence of 10% palladium on carbon catalyst (35% aqueous paste) and then filtered. The filtrate was evaporated to dryness leaving a residue which was stripped several times with diethyl ether to give 1.6 g (97%) of the title compound as a solid.

HPLC retention time=6.9 minutes (system C).
1H NMR (DMSO-d6)δ 4.44 (t, 1H).

EXAMPLE 27

(R)-N-(2-(3-(3-Methoxyphenyl)-3-(2-methylphenyl)-2-propen-1-yloxy)ethyl)-3-piperidinecarboxylic acid hydrochloride A solution of ethyl magnesium bromide in diethyl ether (58 ml, 3 M) was added dropwise at room temperature to a mixture of 3-methoxy benzonitrile (21.2 g, 0.159 mol) and dry THF (250 ml). When addition was complete the mixture was stirred for 1 h at room temperature, 3 h at 40° C. and finally stirred overnight at room temperature. Water (250 ml) was added followed by a saturated ammonium chloride solution (250 ml) and the mixture was stirred for 1 h at room temperature. The phases were separated and the aqueous phase was extracted with ethyl acetate (100 ml). The combined organic phases was dried over magnesium sulphate and the solvent evaporated in vacuo to give 25.9 g (99%) of 3'-methoxypropiophenone.

To a solution of 2-methylphenyl magnesium bromide (prepared from 4.9 g magnesium turnings and 24 ml of 2-bromotoluene) in dry THF (300 ml) was added dropwise a solution of 3'-methoxypropiophenone (25.9 g, 0.16 mol) in dry THF (200 ml). When addition was complete the mixture was heated at reflux temperature for 2 h. Water (250 ml) was added followed by a saturated ammonium chloride solution (250 ml) and the mixture was left overnight. A 4 N hydrochloric acid solution was added until a clear solution was obtained and the phases was separated. The organic phase was dried over magnesium sulphate and the solvent evaporated in vacuo. The residue was submitted to flash chromatography on silica gel (690 g) using a gradient of n-heptane in ethyl acetate to give 28.2 g (55%) of 1-(3-methoxyphenyl)-1-(2-methylphenyl)-1-propanol. A mixture of 1-(3-methoxyphenyl)-1-(2-methylphenyl)-1-propanol (26.2 g, 0.10 mol), isopropanol (300 ml) and a 6 N solution of sulphuric acid (150 ml) was stirred at room temperature for 2 h. The reaction mixture was neutralised with a 4 N sodium hydroxide solution and extracted with ethyl acetate (2×200 ml). The combined organic phases was dried over magnesium sulphate and the solvent was evaporated in vacuo. The residue was submitted to flash chromatography on silica gel (800 g) using n-heptane as eluent to give 18.4 g (76%) of 1-(3-methoxyphenyl)-1-(2-methylphenyl)-1-propene.

A mixture of 1-(3-methoxyphenyl)-1-(2-methylphenyl)-1-propene (18.3 g, 0.077 mol), carbon tetrachloride (80 ml), benzoylperoxide (0.15 g) and N-bromosuccinimide (14.2 g, 0.080 mol) was heated at reflux temperature for 5 h. The reaction mixture was left overnight at room temperature, filtered and the filtrate was evaporated in vacuo to give 3-bromo-1-(3-methoxyphenyl)-1-(2-methylphenyl)-1-propene in a quantitative yield.

A solution of n-butyllithium in hexanes (32.2 ml, 2.5 M) was added dropwise under a nitrogen atmosphere to ethylene glycol (60 ml) at 10° C. When addition was complete the mixture was stirred for 0.5 h at room temperature. A solution of 3-bromo-1-(3-methoxyphenyl)-1-(2-methylphenyl)-1-propene (24.4 g, 77 mmol) in toluene (50 ml) was added and the reaction mixture was stirred at room temperature for 4 days and at 65° C. for 6 h. The solvent was evaporated in vacuo, water (250 ml) was added and the mixture was extracted with ethyl acetate (2×200+100 ml). The combined organic phases was dried over magnesium sulphate and the solvent was evaporated in vacuo. Flash chromatography of the residue on silica gel (320 g) using a mixture of cyclohexane and ethyl acetate gradient as eluent provided 16.6 g (72%) of 2-(3-(3-methoxyphenyl)-3-(2-methylphenyl)-2-propen-1-yloxy)ethanol.

A solution of 2-(3-(3-methoxyphenyl)-3-(2-methylphenyl)-2-propen-1-yloxy)ethanol (7.6 g, 25.4 mmol) in dry toluene (150 ml) was cooled on an ice-bath and a solution of n-butyllithium in hexanes (11.2 ml, 2.5 M) was added dropwise. The reaction mixture was stirred for 0.5 h at room temperature and p-toluenesulphonyl chloride (5.3 g, 28 mmol) was added. The mixture was stirred at room temperature for 1.5 h. Ethyl (R)-3-piperidinecarboxylate (8.8 g, 50 mmol) and potassium carbonate (7.7 g, 50 mmol) were added and the mixture was stirred at room temperature for 4 h. Toluene (100 ml), acetone (50 ml) and potassium iodide (1.7 g) were added and the reaction mixture was heated at 75° C. for 84 h. The cooled reaction mixture was filtered and the solvent evaporated in vacuo. The residue was submitted to flash chromatography on silica gel (250 g) using a mixture of n-heptane and ethyl acetate (4:1) as eluent to give 7.5 g (68%) of (R)-N-(2-(3-(3-methoxyphenyl)-3-(2-methylphenyl)-2-propen-1-yloxy)ethyl)-3-piperidinecarboxylic acid ethyl ester as an oil. TLC: rf=0.20 (SiO$_2$; ethyl acetate).

(R)-N-(2-(3-(3-Methoxyphenyl)-3-(2-methylphenyl)-2-propen-1-yloxy)ethyl)-3-piperidinecarboxylic acid ethyl ester (7.3 g, 16.7 mmol) was dissolved in ethanol (50 ml) and a 50% sodium hydroxide solution (6.7 g) was added. The reaction mixture was stirred at room temperature for 2 h and water (250 ml) was added. The mixture was extracted with diethyl ether (2×25 ml) and the aqueous phase was neutralised with concentrated hydrochloric acid solution. Part of the solvent was evaporated in vacuo and pH was adjusted to 1 with concentrated hydrochloric acid. The acidic aqueous solution was extracted with dichloromethane (2×250+150 ml). The combined organic extracts was dried over magnesium sulphate and the solvent evaporated in vacuo. The residue was crystallised from acetone and then recrystallised from a mixture of toluene and methanol to give 5.1 g (68%) of the title compound.

M.P. 180°–182° C. Calculated for C$_{25}$H$_{32}$ClNO$_4$: C, 67.3%; H, 7.2%; Cl, 8.0%; N, 3.1% Found: C, 67.3%; H, 7.4%; Cl, 7.9%; N, 3.0%

$^1$H NMR (DMSO-d$_6$)δ 3.85 (d, 2H), 6.43 (t, 1H).

EXAMPLE 28

(R)-N-(2-(3-(3-Methoxyphenyl)-3-(2-methylphenyl)-1-propyloxy)ethyl)-3-piperidinecarboxylic acid hydrochloride The acid prepared in Example 27 (2.0 g, 4.5 mmol) was dissolved into methanol (50 ml) and stirred under an atmosphere of hydrogen for 1 h at room temperature in the presence of 10% palladium on carbon catalyst (65% aqueous paste) and then filtered. The filtrate was evaporated to dryness leaving a solid residue which was recrystallised from a mixture of acetone and ethyl acetate to give 0.30 g (23%) of the title compound.

M.P 132°–138° C. Calculated for C$_{25}$H$_{34}$ClNO$_4$, ½H$_2$O: C, 65.7%; H, 7.7%; Cl, 7.8%; N, 3.1% Found: C, 65.4%; H, 7.6%; Cl, 8.2%; N, 2.9% $^1$H NMR (DMSO-d$_6$)δ 4.23 (t, 1H).

EXAMPLE 29

(R)-N-(2-(3,3-Bis(2-Methylphenyl)-2-propen-1-yloxy)ethyl)-3-piperidinecarboxylic acid hydrochloride A solution of n-butyllithium in hexanes (14 ml, 2.5 M) was added dropwise under a nitrogen atmosphere to ethylene glycol (28 ml) at 0° C. When addition was complete the mixture was stirred 0.5 h at room temperature. 3-Bromo-1,1-bis(2-methylphenyl)-1-propene (10.5 g, 35 mmol, prepared in a similar way to the method described in Example 23) was added and the reaction mixture was stirred at room temperature for 12 h and at 70° C. for 24 h. Water (100 ml) was added and the mixture was extracted with ethyl acetate (3×100 ml). The combined organic extracts were dried over magnesium sulphate and the solvent evaporated in vacuo. Flash chromatography of the residue on silica gel (250 g) using a mixture of n-heptane and ethyl acetate (10:1) as eluent provided 3.0 g (30%) of 2-(3,3-bis(2-methylphenyl)-2-propen-1-yloxy)ethanol.

A solution of 2-(3,3-bis(2-methylphenyl)-2-propen-1-yloxy)ethanol (3.0 g, 10.7 mmol) in dry toluene (100 ml) was cooled on an ice-bath and a solution of n-butyllithium in hexanes (4.7 ml, 2.5 M) was added dropwise. The reaction mixture was stirred for 15 minutes at room temperature and p-toluenesulphonyl chloride (2.2 g, 11.7 mmol) was added. The mixture was stirred at room temperature for 2.5 h. Ethyl (R)-3-piperidinecarboxylate (3.4 g, 21.4 mmol) and potassium carbonate (2.9 g, 21.4 mmol) were added and the mixture was stirred at room temperature for 1 h and then at 75° C. for 12 h. Potassium iodide (0.9 g) was added and the mixture was heated at reflux temperature for 15 h. The cooled reaction mixture was filtered and the solvent evaporated in vacuo. Flash chromatography of the residue on silica gel (150 g) using a gradient of n-heptane in ethyl acetate as eluent afforded 2.2 g (49%) of (R)-N-(2-(3,3-bis(2-methylphenyl)-3-propen-1-yl)oxyethyl)-3-piperidinecarboxylic acid ethyl ester as an oil. TLC: rf=0.55 (SiO$_2$; ethyl acetate/methanol=9:1).

(R)-N-(2-(3,3-bis(2-methylphenyl)-2-propen-1-yloxy)-ethyl)-3-piperidinecarboxylic acid ethyl ester (2.2 g, 5.1 mmol) was dissolved in ethanol (20 ml) and 12 N sodium hydroxide solution (2.1 ml) was added. The reaction mixture was stirred at room temperature for 0.5 h. Water (200 ml) was added and the mixture was extracted with diethyl ether (5×20 ml). pH was adjusted to 1 with concentrated hydrochloric acid and the mixture was extracted with dichloromethane (2×250+100 ml). The combined organic extracts were dried over magnesium sulphate and the solvent was evaporated in vacuo to give a residue which was crystallised from ethyl acetate and finally recrystallised from a mixture of methanol and toluene. This provided 1.4 g (66%) of the title compound.

M.P. 188°–190° C. Calculated for C$_{25}$H$_{32}$ClNO$_3$: C, 69.8%; H, 7.5%; N, 3.3% Found: C, 70.0%; H, 7.7%; N, 3.2%

$^1$H NMR (DMSO-d$_6$)δ 3.95 (d, 2H,); 5.90 (t, 1H).

EXAMPLE 30

(R)-N-(2-(3,3-Bis(2-Methylphenyl)-1-propyloxy)ethyl)-3-piperidinecarboxylic acid hydrochloride The acid prepared in Example 29 (1.1 g, 2.6 mmol) was dissolved in methanol (25 ml) and stirred under an atmosphere of hydrogen for 1 h at room temperature in the presence of 10% palladium on carbon catalyst (35% aqueous paste) and then filtered. The filtrate was evaporated to dryness leaving a residue which was treated with a mixture of ethyl acetate and acetone and filtered to give a solid which was recrystallised from a mixture of methanol and toluene to give 0.75 g (67%) of the title compound as a solid.

M.P. 193°–195.5° C. Calculated for C$_{25}$H$_{34}$ClNO$_3$: C, 69.5%; H, 7.9%; N, 3.2% Found: C, 69.6%; H, 8.3%; N, 3.2%

$^1$H NMR (DMSO-d$_6$)δ 4.38 (t, 1H).

EXAMPLE 31

(R)-N-(3-(3,3-Bis(2-Methylphenyl)-2-propen-1-yloxy)-1-propyl)-3-piperidinecarboxylic acid hydrochloride A solution of n-butyllithium in hexanes (15.2 ml, 2.5 M) was added dropwise under a nitrogen atmosphere to 1,3- propanediol (31 ml) on an ice-bath. When addition was complete the mixture was stirred 0.5 h at room temperature. 3-Bromo-1,1-bis(2-methylphenyl)-1-propene (11.5 g, 38 mmol, prepared in a similar way to the method described in Example 23) was added and the reaction mixture was stirred at room temperature for 48 h and at 75° C. for 36 h. Water (100 ml) was added and the mixture was extracted with ethyl acetate (100 ml). The phases were separated and the organic phase was washed with water (2×50 ml), dried over magnesium sulphate and the solvent evaporated in vacuo. Flash chromatography of the residue on silica gel (300 g) using a gradient of n-heptane in ethyl acetate as eluent provided 3.5 g (31 %) of 3-(3,3-bis(2-methyl phenyl)-2-propen-1-yloxy)-1-propanol.

A solution of 3-(3,3-bis(2-methylphenyl)-2-propen-1-yloxy)-1-propanol (3.45 g, 11.6 mmol) in dry toluene (150 ml) was cooled in an ice-bath and a solution of n-butyllithium in hexanes (5.1 ml, 2.5 M) was added dropwise. The reaction mixture was stirred for 15 minutes at room temperature and p-toluenesulphonyl chloride (2.44 g, 12.8 mmol) was added. The mixture was stirred at room temperature for 3 h. Ethyl (R)-3-piperidinecarboxylate (4.5 g, 23.3 mmol) and potassium carbonate (3.2 g, 23.3 mmol) were added and the mixture was stirred at room temperature for 0.5 h and then at 75° C. for 12 h. Potassium iodide (1.0 g) and acetone (40 ml) were added and the mixture was heated at reflux temperature for 15 h. Acetone (50 ml) was added and the cooled reaction mixture was filtered and the solvent evaporated in vacuo. Flash chromatography of the residue on silica gel (280 g) using a gradient of n-heptane in ethyl acetate as eluent afforded 2.6 g (52%) of (R)-N-(3-(3,3-bis(2-methylphenyl)-2-propen-1-yloxy)-1-propyl)3-piperidinecarboxylic acid ethyl ester as an oil. TLC: rf=0.52 (SiO$_2$; methanol/ethyl acetate=1:9).

(R)-N-(3-(3,3-Bis(2-Methylphenyl)-2-propen-1-yloxy)-1-propyl)-3-piperidinecarboxylic acid ethyl ester (2.6 g, 6.0 mmol) was dissolved in ethanol (20 ml) and a 12 N sodium hydroxide solution (2.5 ml) was added. The reaction mixture was stirred at room temperature for 0.5 h. Water (250 ml) was added and the mixture was extracted with diethyl ether (2×50 ml). A 2 M hydrochloric acid solution was added to the aqueous phase until acid was measured at pH 1 and the mixture was extracted with dichloromethane (3×200 ml). The combined organic extracts were dried over magnesium sulphate and the solvent was evaporated in vacuo to give a residue which was treated with a mixture of ethyl acetate and acetone and finally recrystallised from a mixture of methanol and toluene. This provided 1.3 g (49%) of the title compound. TLC: rf=0.47 (SiO$_2$; methanol/dichloromethane=1:1).

M.P. 156°–158° C. Calculated for C$_{26}$H$_{34}$ClNO$_3$: C, 70.3%; H, 7.7%; N, 3.2% Found: C, 70.3%; H, 7.7%; N, 2.9%

$^1$H NMR (DMSO-d$_6$)δ 3.89 (d, 2H); 5.87 (t, 1H).

EXAMPLE 32

(R)-N-(3-(3,3-Bis(2-Methylphenyl)-1-propyloxy)-1-propyl)-3-piperidinecarboxylic acid hydrochloride The acid prepared in Example 31 (0.75 g, 1.7 mmol) was dissolved in methanol (25 ml) and stirred under an atmosphere of hydrogen for 1 h at room temperature in the presence of 10% palladium on carbon catalyst (35% aqueous paste) and then filtered. The filtrate was evaporated to dryness leaving a residue which was treated with a mixture of ethyl acetate and acetone and filtered to give a solid which was recrystallised from toluene to give 0.20 g (26%) of the title compound as a solid. TLC: rf=0.39 (SiO$_2$; methanol/dichloromethane=1 1).

M.P. 186°–187° C. Calculated for C$_{26}$H$_{36}$ClNO$_3$: C, 70.0%; H, 8.1%; N, 3.1% Found: C, 69.7%; H, 8.2%; N, 3.0%

$^1$H NMR (DMSO-d$_6$)δ 4.39 (t, 1H).

EXAMPLE 33

(R)-N-(2-(3-(3-Methoxyphenyl)-3-phenyl-2-propen-1-yloxy)ethyl)-3-piperidinecarboxylic acid A solution of n-butyllithium in hexanes (76 ml, 2.5 M) was added dropwise under a nitrogen atmosphere to ethylene glycol (30 ml) at 10° C. When addition was complete the mixture was stirred for 0.5 h at room temperature. 3-Bromo-1-(3-methoxyphenyl)-1-phenyl-1-propene (57.5 g, 0.19 mol, prepared in a similar way to the method described in Example 23) in toluene (40 ml) was added and the reaction mixture was stirred at room temperature for 84 h. The mixture was poured into water (400 ml) and extracted with ethyl acetate (250+100 ml). The combined organic extracts was washed with water, brine and dried over sodium sulphate. The solvent was evaporated in vacuo to give a residue which was stripped with methanol and dichloromethane successively. This afforded 53.1 g (99%) of 2-(3-(3-methoxyphenyl)-3-phenyl-2-propen-1-yloxy)ethanol. TLC: rf=0.41 (SiO$_2$; chloroform/methanol=19:1).

A mixture of 2-(3-(3-methoxyphenyl)-3-phenyl-2-propen-1-yloxy)ethanol (52 g, 0.18 mol) and triethylamine (46 g, 0.46 mol) in dry toluene (200 ml) kept under a nitrogen atmosphere was cooled below 10° C. and a solution of methanesulphonyl chloride (41.7 g, 0.36 mol) in dry toluene (200 ml) was added dropwise keeping the temperature below 10° C. When addition was complete the reaction mixture was stirred for 1 h at 5° C. and then for 0.5 h at approximately 15° C. Water was added (250 ml) and the mixture was stirred at room temperature for 0.5 h. The separated organic phase was washed with a 5% sodium bicarbonate solution, brine and dried over sodium sulphate. The mixture was filtered and the filtrate was reduced to approximately 500 ml in vacuo. Ethyl (R)-3-piperidinecarboxylate (57.2 g, 0.36 mol) and potassium carbonate (62.8 g, 0.46 mol) were added and the mixture was heated at reflux temperature for 48 h. The cooled reaction mixture was filtered and the solid was washed with toluene and ethyl acetate successively. The combined organic filtrates was evaporated in vacuo to an oily residue which was dissolved into ethyl acetate (250 ml). Water (150 ml) was added and pH was adjusted to 4 with 10% citric acid solution. The phases were separated and the organic phase was washed with water (150 ml). The combined aqueous phases was extracted with ethyl acetate (150 ml) and then discarded. The combined organic phases was washed with a 5% sodium bicarbonate solution, brine, dried over sodium sulphate and the solvent evaporated in vacuo. The residue was dissolved in toluene (150 ml) and a solution of tartaric acid (42 g) in water (120 ml) was added. The phases were separated and the organic phase was extracted with another solution of tartaric acid (12 g) in water (50 ml). The combined aqueous extracts was extracted with ethyl acetate (200 ml) which was discarded. Ethyl acetate (200 ml) was added to the acidic aqueous phase which was made alkaline with excess of a sodium bicarbonate solution. The separated organic phase was washed with brine and dried over sodium sulphate. The solvent was evaporated in vacuo to give 46.6 g (60% of (R)-N-(2-(3-(3- methoxyphenyl)-3-phenyl-2-propen-1-yloxy)ethyl)-3-piperidinecarboxylic acid ethyl ester as an oil. TLC: rf=0.36 (SiO$_2$; chloroform/methanol/acetic acid=20:2:1). (R)-N-(2-(3-(3-Methoxyphenyl)-3-phenyl-2-propen-1-yloxy)ethyl)-3-piperidinecarboxylic acid ethyl ester (25 g, 59 mmol) was dissolved into 96% ethanol (275 ml) and a 12 N sodium hydroxide solution (22 ml) was added. The reaction mixture was stirred at room temperature for 3.5 h. The solvent was evaporated in vacuo and dichloromethane was added (250 ml). A concentrated hydrochloric acid solution (29.5 ml) was added with cooling of the reaction vessel in an ice-bath. The phases were separated and the organic phase was dried over sodium sulphate. The solvent was evaporated in vacuo to give a residue which was dissolved into water (250 ml). The aqueous solution was extracted with toluene (3×50 ml) and diethyl ether (50 ml). The organic extracts were discarded and from the aqueous phase water was evaporated in vacuo to give 25 g (98%) of the title compound as an oil. TLC: rf=0.23 (SiO$_2$; chloroform/methanol/acetic acid=80:15:5).

HPLC retention time=12.0 and 12.4 minutes (system B).

$^1$H NMR (DMSO-d$_6$)δ 4.02 (t, 2H); 6.25 (dt, 1H).

EXAMPLE 34

(R)-N-(2-(3-(3-Methoxyphenyl)-3-phenyl-1-propyloxy)-ethyl)-3-piperidinecarboxylic acid fumarate The acid prepared in Example 33 (20.0 g, 46.3 mmol) was dissolved in methanol (300 ml) and stirred under an atmosphere of hydrogen for 1 h at room temperature in the presence of 10% palladium on carbon catalyst (35% aqueous paste) and then filtered. The filtrate was evaporated to dryness leaving a residue which was stripped with dichloromethane to give 19.2 g (96%) of the title compound as a foam. The material was submitted to reverse phase column chromatography using a mixture of methanol, a 2 M aqueous ammonia solution and a 3% aqueous sodium chloride solution (60:10:30) as eluent. This afforded 12.0 g (53%) of the title compound as a solid.

HPLC retention time=11.0 minutes (system B).

$^1$H NMR (DMSO-d$_6$)δ 4.05 (t, 1H).

EXAMPLE 35

(R)-N-(2-(3,3-Bis(4-Chlorophenyl)-2-propen-1-yloxy)-ethyl)-3-piperidinecarboxylic acid ethyl ester A solution of n-butyllithium in hexanes (15.0 ml, 2.5 M) was added dropwise under a nitrogen atmosphere to ethylene glycol (30 ml) at 10° C. When addition was complete the mixture was stirred for 0.5 h at room temperature. 3-Bromo- 1,1-bis(4-chlorophenyl)-1-propene (13.0 g, 38 mmol, prepared similarly to the method described in Example 23) was added and the reaction mixture was stirred at room temperature for 72 h. The mixture was poured into water (100 ml) and extracted with ethyl acetate (2×75 ml). The combined organic extracts was dried over sodium sulphate and the solvent evaporated in vacuo. Flash chromatography of the residue on silica gel (200 g) using a mixture of n-heptane and ethyl acetate (3:2) as eluent provided 8.1 g (66%) of 2-(3,3-bis(4-chlorophenyl)-2-propen-1-yloxy)ethanol, M.P. 93°-95° C.

A solution of 2-(3,3-bis(4-chlorophenyl)-2-propen-1-yloxy)ethanol (4.0 g, 12.4 mmol) in dry THF (25 ml) kept under a nitrogen atmosphere was cooled to 10° C. and a solution of n-butyllithium in hexanes (5.4 ml, 2.5 M) was added dropwise. The reaction mixture was stirred for 15 minutes at room temperature and p-toluenesulphonyl chloride (2.6 g, 13.8 mmol) was added. The mixture was stirred at room temperature for 1 h. Ethyl (R)-3-piperidinecarboxylate (1.9 g, 12.1 mmol) and potassium carbonate (3.4 g, 24.6 mmol) were added and the mixture was heated at reflux temperature for 18 h. To the cooled reaction mixture THF (50 ml) was added. The mixture was filtered and the solvent evaporated in vacuo. Flash chromatography of the residue on silica gel (100 g) using a mixture of n-heptane and ethyl acetate (3:2) as eluent provided 0.6 g (11%) of the title compound as an oil. $^1$H NMR (CDCl$_3$)δ 4.02 (d, 2H); 6.20 (t, 1H).

EXAMPLE 36

(R)-N-(2-(3,3-Bis(4-Chlorophenyl)-2-propen-1-yloxy)-ethyl)-3-piperidinecarboxylic acid hydrochloride The ester prepared in Example 35 (0.6 g, 1.3 mmol) was dissolved in ethanol (10 ml) and a 12 N sodium hydroxide solution (0.5 ml) was added. The reaction mixture was stirred at room temperature for 5 h. A concentrated hydrochloric acid solution was added with cooling on an ice-bath until pH 1 and dichloromethane (300 ml) was added. The resulting emulsion was dried over sodium sulphate ant the solvent evaporated in vacuo to give a residue which was agitated with acetone. This afforded 0.3 g (50%) of the title compound as a solid.

M.P. 203°-204° C. Calculated for C$_{23}$H$_{26}$Cl$_3$NO$_3$·H$_2$O: C, 56.5%; H, 5.8%; Cl, 7.3%; N, 2.9% Found: C, 56.6%; H, 5.5%; Cl, 7.4%; N, 2.6%

$^1$H NMR (DMSO-d$_6$)δ 4.02 (d, 2H); 6.30 (t, 1H).

EXAMPLE 37

(R)-N-(2-(3-(3-Chlorophenyl)-3-phenyl-2-propen-1-yloxy)ethyl)-3-piperidinecarboxylic acid A solution of n-butyllithium in hexanes (75 ml, 2.5 M) was added dropwise under a nitrogen atmosphere to ethylene glycol (150 ml) at 5° C. When addition was complete the mixture was stirred at room temperature for 0.5 h. 3- Bromo-1-(3-chlorophenyl)-1-phenyl-1-propene (58.5 g, 0.19 mol, prepared in a similar way to the method described in Example 22) was added and the reaction mixture was stirred at room temperature for 96 h. The reaction mixture was poured into water (200 ml) and extracted with ethyl acetate (2×200 ml). The combined organic extracts was washed with brine and dried over sodium sulphate. The solvent was evaporated in vacuo to give a residue which was stripped with methanol and dichloromethane sucessively. This afforded 52.2 g (96%) of 2-(3-(3-chlorophenyl)-3-phenyl-2-propen-1-yloxy)ethanol. TLC: rf=0.10 (SiO$_2$; n-heptane/ethyl acetate=4:1).

A mixture of 2-(3-(3-chlorophenyl)-3-phenyl-2-propen-1-yloxy)ethanol (52.2 g, 0.18 mol) and triethylamine (45.7 g, 0.45 mol) in dry toluene (200 ml) kept under a nitrogen atmosphere was cooled to 5° C. and a solution of methanesulphonyl chloride (41.4 g, 0.36 mol) in dry toluene (200 ml) was added dropwise keeping the temperature below 10° C. When addition was complete the reaction mixture was stirred for 1 h at 5° C. Water was added (250 ml) and the mixture was stirred at room temperature for 10 minutes. The phases were separated and the aqueous phase was extracted with a small portion of toluene. The combined organic extracts were washed with brine and dried over sodium sulphate. The mixture was filtered and the filtrate was reduced in vacuo to approximately 500 ml. Ethyl (R)-3-piperidinecarboxylate (56.8 g, 0.36 mol) and potassium carbonate (49.9 g, 0.36 mol) were added and the mixture was heated at reflux temperature for 7 days. The cooled reaction mixture was poured into water (200 ml) and extracted with ethyl acetate (2×200 ml). The combined organic extracts were washed with a sodium citrate buffer solution (pH 5) and then extracted with a 34% aqueous tartaric acid solution (3×100 ml). The combined acidic aqueous extracts were poured into a mixture of ice water (3 l) and ethyl acetate (400 ml). Sodium hydroxide pellets (27.2 g) was added until pH was measured at ca. 4 and the phases were separated. The organic phase was washed with a 5% sodium bicarbonate solution (3×150 ml) and dried over sodium sulphate. The solvent was evaporated in vacuo to give 57.5 g (74%) of (R)-N-(2-(3-(3-chlorophenyl)-3-phenyl-2-propen-1-yloxy)ethyl)-3-piperidinecarboxylic acid ethyl ester as an oil. TLC: rf=0.45 (SiO2; dichloromethane/methanol/acetic acid=20:2:1).

(R)-N-(2-(3-(3-Chlorophenyl)-3-phenyl-2-propen-1-yloxy)ethyl)-3-piperidinecarboxylic acid ethyl ester (3.0 g, 7.0 mmol) dissolved in 96% ethanol (10 ml) and a 12 N sodium hydroxide solution (1.75 ml) was added. The reaction mixture was stirred at room temperature for 5 h. The solvent was evaporated in vacuo and dichloromethane was added (100 ml). A concentrated hydrochloric acid solution (2.9 ml) was added with cooling on an ice-bath. The phases were separated, and from the organic phase the solvent was evaporated in vacuo. Water (100 ml) was added to the residue and the aqueous solution was washed with small portions of ethyl acetate. The aqueous phase was reduced in vacuo to approx. 50 ml and dichloromethane (250 ml) was added. A 4 N sodium hydroxide solution was added until the pH was measured as 8.3. The phases were separated and the organic phase was dried over sodium sulphate. The solvent was evaporated in vacuo to give 2.7 g (96%) of the title compound.

HPLC retention time=16.0 and 16.3 minutes (system B).

$^1$H NMR (CDCl$_3$)$\delta$ 4.02 (t, 2H); 6.20 (dt, 1H).

EXAMPLE 38

(R)-N-(2-(3-(3-Methylphenyl)-3-phenyl-2-propen-1-yloxy)ethyl)-3-piperidinecarboxylic acid A solution of n-butyllithium in hexanes (73 m, 2.5 M) was added dropwise under a nitrogen atmosphere to ethylene glycol (150 ml) at 5° C. When addition was complete the mixture was stirred for 0.5 h at room temperature. 3-Bromo-1-(3-methylphenyl)-1-phenyl-1-propene (52 g, 0.18 mol, prepared in a similar way to that described in Example 23) was added and the reaction mixture was stirred at room temperature for 5 days. The reaction mixture was poured into water (200 ml) and extracted with diethyl ether (2×200 ml). The combined organic extracts was washed with brine and dried over magnesium sulphate. The solvent was evaporated in vacuo to give a residue which was submitted to flash chromatography on silica gel (900 g) using a mixture of n-heptane and ethyl acetate as eluent. This afforded 31 g (64%) of 2-(3-(3-methylphenyl)-3-phenyl-2-propen-1yloxy)ethanol. TLC: rf=0.08 (SiO2; n-heptane/ethyl acetate=4:1).

A mixture of 2-(3-(3-methylphenyl)-3-phenyl-2-propen-1-yloxy)ethanol (16 g, 60 mmol) and triethylamine (15.1 g, 149 mmol) in dry toluene (75 ml) kept under a nitrogen atmosphere was cooled to 5° C. and a solution of methanesulphonyl chloride (13.7 g, 119 mmol) in dry toluene (75 ml) was added dropwise keeping the temperature below 10° C. When addition was complete the reaction mixture was stirred for 1.5 h at 5° C. Water was added (100 ml) and the mixture was stirred at room temperature for 0.5 h. The phases were separated and the aqueous phase was extracted with a small portion of toluene. The combined organic extracts was washed with brine, dried over sodium sulphate and filtered. To the filtrate was added ethyl (R)-3-piperidinecarboxylate (10.3 g, 66 mmol) and potassium carbonate (9.9 g, 72 mmol) and the mixture was heated at reflux temperature for 6 days. Another portion of ethyl (R)-3-piperidinecarboxylate (5.3 g) was added and the mixture was heated at reflux temperature for another 24 h. The reaction mixture was poured into ice water (200 ml) and extracted with ethyl acetate (2×200 ml). The combined organic extracts was washed with a sodium citrate buffer solution (2×100 ml, pH 5) and then extracted with a 5% aqueous citric acid solution (4×100 ml). Toluene (120 ml) was added to the combined acidic extracts and sodium hydroxide pellets was added to the mixture until the pH was measured at 8.5. The phases were separated and the organic phase was dried over sodium sulphate. The solvent was evaporated in vacuo to give 9.4 g (39%) of (R)-N-(2-(3-(3-methylphenyl)-3-phenyl-2-propen-1-yloxy)ethyl)-3-piperidinecarboxylic acid ethyl ester as an oil. TLC: rf=0.50 (SiO2; dichloromethane/methanol/acetic acid=20:2:1).

(R)-N-(2-(3-(3-Methylphenyl)-3-phenyl-2-propen-1-yloxy)ethyl)-3-piperidinecarboxylic acid ethyl ester (3.5 g, 8.6 mmol) was dissolved in 96% ethanol (10 ml) and a 12 N sodium hydroxide solution (2.2 ml) was added. The reaction mixture was stirred at room temperature for 4 h. The solvent was evaporated in vacuo and dichloromethane (100 ml) and water (10 ml) were added. A concentrated hydrochloric acid solution (3.4 ml) was added with cooling on an ice-bath. The phases were separated and from the organic phase the solvent was evaporated in vacuo. Water (100 ml) was added to the residue and the aqueous solution was washed with small portions of ethyl acetate. The aqueous phase was reduced to approx. 10 ml in vacuo. Dichloromethane (250 ml) and water (40 ml) were added and pH of the solution was adjusted to 8.5 with a 4 N sodium hydroxide solution. The phases were separated and the organic phases was dried over sodium sulphate. The solvent was evaporated in vacuo to give 2.4 g (74%) of the title compound.

HPLC retention time=17.8 minutes (system B).
$^1$H NMR (CDCl$_3$)$\delta$ 4.03 (dd, 2H); 6.17 (t, 1H).

EXAMPLE 39

(R)-N-(2-(3-(3-Methylphenyl)-3-phenyl-1-propyloxy)-ethyl)-3-piperidinecarboxylic acid The acid prepared in Example 38 (8.2 g, 21.6 mmol) was dissolved in methanol (150 ml) and stirred under an atmosphere of hydrogen for 1 h at room temperature in the presence of 10% palladium on carbon catalyst (35% aqueous paste) and then filtered. The filtrate was evaporated to dryness leaving a residue which was dissolved into dichloromethane and dried over sodium sulphate. The solvent was evaporated in vacuo to give 2.3 g (28%) of the title compound as a foam.

HPLC retention time=16.0 minutes (system B).

$^1$H NMR (DMSO-d$_6$) δ 4.05 (t, 1H).

We claim:

1. A compound of formula I

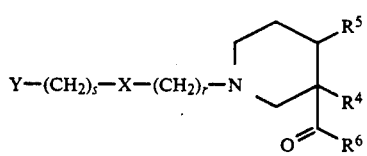

wherein Y is

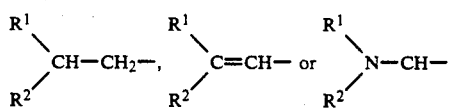

wherein
R$^1$ and R$^2$ independently are C$_{3-8}$-cycloalkyl, phenyl or thienyl, each of which may be optionally substituted with halogen, trifluoromethyl, C$_{1-6}$-alkyl or C$_{1-6}$-alkoxy;
X is CH$_2$ or O;
R$^4$ and R$^5$ each represents hydrogen or may together represent a bond; and
R$^6$ is OH or C$_{1-8}$-alkoxy;
r is 2, 3 or 4;
s is 1, 2 or 3;
provided that X is not —CH$_2$— when Y is

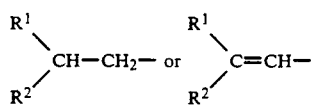

or a geometric or optical isomer thereof; or a pharmaceutically acceptable salt thereof.

2. The compound according to claim 1, wherein Y is

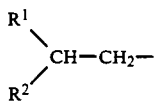

X is O; and R$^6$ is OH.

3. The compound according to claim 1, wherein Y is

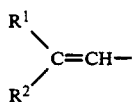

X is O; and R$^6$ is OH.

4. The compound according to claim 1, wherein Y is

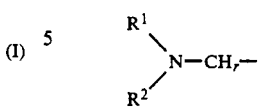

X is O; and R$^6$ is OH.

5. The compound according to claim 1, wherein Y is

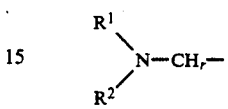

X is CH$_2$; and R$^6$ is OH.

6. The compound according to claim 1 which is
(R)-N-(2-(3,3-Diphenyl-1-propyloxy)ethyl)3-piperidinecarboxylic acid;
N-(2-(3,3-Diphenyl-propyloxy)ethyl)-1,2,5,6-tetrahydro-3-pyridinecarboxylic acid;
(R)-N-(2-(3-Phenyl-3-(3-(trifluoromethyl)phenyl)-1-propyloxy)-ethyl)-3-piperidinecarboxylic acid;
(R)-N-(2-(3,3-Bis(4-Chlorophenyl)-1-propyloxy)ethyl-3-piperidinecarboxylic acid;
(R)-N(2-(3-(3-Methoxyphenyl)-3-(2-methylphenyl)-1-propyloxy)ethyl)-3-piperidinecarboxylic acid;
(R)-N-(3-(3,3-Bis(2-Methylphenyl)-2-propen-1-yloxy)-1-propyl)-3-piperidinecarboxylic acid; or a pharmaceutically acceptable salt thereof.

7. A pharmaceutical composition for treating muscular and movement disorders, pain, anxiety, depression or sleeping disorders comprising an effective amount of a compound according to claim 1 together with a pharmaceutically acceptable carrier or diluent.

8. The pharmaceutical composition according to claim 7, wherein the muscular and movement disorder is epilepsy.

9. The pharmaceutical composition according to claim 7 comprising between 0.5 mg and 1000 mg of the compound according to claim 8 per unit dose.

10. A method of treating muscular and movement disorders, pain, anxiety, depression or sleeping disorders in a subject in need thereof comprising administering to said subject an effective amount of a compound according to claim 1.

11. The method according to claim 10, wherein the muscular and movement disorder is epilepsy.

12. A method of treating muscular and movement disorders, pain, anxiety, depression or sleeping disorders in a subject in need thereof comprising administering to said subject a pharmaceutical composition according to claim 7.

13. The method according to claim 2, wherein the muscular and movement disorders is epilepsy.

* * * * *